United States Patent [19]

Troxell

[11] Patent Number: 4,982,601

[45] Date of Patent: Jan. 8, 1991

[54] METHOD FOR THE VISUAL DISPLAY OF THE MIGRATION OF BOWLING LANE OIL DURING PLAY

[76] Inventor: James D. Troxell, P.O. Box 123, Cuyahoga Falls, Ohio 44222

[21] Appl. No.: 446,178

[22] Filed: Dec. 5, 1989

[51] Int. Cl.⁵ ............................................ B23Q 17/09
[52] U.S. Cl. ...................................................... 73/104
[58] Field of Search .............................. 73/104, 865.8; 250/301–303, 458.1, 459.1, 461.1, 462.1, 375; 434/388, 392

[56] References Cited

U.S. PATENT DOCUMENTS 3,341,705 9/1967 Alburger ............................. 250/302
3,675,015 7/1972 Geib ..................................... 250/302
4,437,010 3/1984 Scheie et al. ........................ 250/302

Primary Examiner—Robert Raevis
Attorney, Agent, or Firm—Renner, Kenner, Greive, Bobak, Taylor & Weber

[57] ABSTRACT

A method for displaying the migration of lane oil over bowling alleys during play comprises the steps of incorporating an additive into the lane oil that is non-discernable when viewed with ambient light; applying the lane oil and incorporated additive to the surfaces of a bowling alley in a conventional manner; and selectively illuminating the surfaces with light from a portion of the electromagnetic spectrum having a wavelength to which the additive is responsive, thereby rendering detectable the presence of the lane oil and the migration thereof over the bowling alley.

11 Claims, 4 Drawing Sheets

METHOD FOR THE VISUAL DISPLAY OF THE MIGRATION OF BOWLING LANE OIL DURING PLAY

TECHNICAL FIELD

The present invention relates to televised bowling tournaments and other bowling activities. More particularly the invention provides a method that enhances the viewing and learning experience for viewers of bowling activities. Used in conjunction with a modest array of equipment, the method provides a much needed illumination of a little understood aspect of the game.

BACKGROUND OF THE INVENTION

Bowling lanes have long been coated with various clear protective coatings to keep them clean and free of ball marks, provide longevity and render a consistent friction coefficient permitting stable ball performance. However, the coatings along are not adequate to achieve these goals. As untreated they will eventually wear away from the constant rotation and sliding of the heavy bowling balls. Many of the balls are also somewhat abrasive and can eventually wear paths on the lane surface. In response to this weakness, oil preparations were introduced to protect the coatings and make lanes consistent.

While all bowling establishments use oils, application is standarized only for PBA tournaments. In those tournaments, the oil is sprayed on the lane across the entire width for a measured distance from the foul line. As the game progresses, the balls carry the oil beyond the application area along paths described by the ball. In championship, televised play, most of the balls are thrown on a path leading to the "pocket". As a result of most bowlers being right-handed, a path of oil grows along the right side of the lane. Spares shots and left-handed bowlers will spread the oil more slowly along the other areas of the lane.

Most professional bowlers are familiar with this oil migration and actually change balls as the game progresses to accommodate the change in lane conditions. Balls with greater friction characteristics are utilized later in the tournament to maintain ball control or hook. Also, balls are selected during the tournament for individual spare shots that travel outside the area deemed by the professional to be dry, or where oils has not yet spread.

Thus, despite the fact that millions of league bowlers regularly watch televised bowling tournaments, not only to be entertained but also to learn to become better bowlers, the existing art and broadcasting technology has failed to provide a method for visually displaying the migration of bowling lane oil during televised broadcasts of bowling activity.

SUMMARY OF THE INVENTION

It is therefore, a primary object of the present invention to provide a relatively inexpensive method for depicting the migration of bowling lane oil for viewers of television broadcasts.

It is another object of the present invention to provide a method utilizing fairly conventional equipment in a novel manner that need not interfere with the players, the viewers or the activity of the game.

It is a further object of the present invention to provide a method that allows visual display of the otherwise colorless paths of lane oil carried and deposited by the bowling ball during play which explains the behavior of balls subsequently played and allows prediction of the path.

It is still another object of the present invention to provide a method as above which can be selectively presented solely to viewers of television and closed circuit broadcasts or to everyone present at the event as well.

These and other objects of the invention, as well as the advantages thereof over existing and prior art forms, which will be apparent in view of the following detailed specifications, are accomplished by means hereinafter described and claimed.

In general, a method embodying the concepts of the present invention for displaying the migration of lane oil over bowling alleys during play comprises the steps of incorporating an additive into the lane oil that is non-discernable when viewed with ambient light; applying the lane oil and incorporated additive to the surfaces of a bowling alley in a conventional manner; and selectively illuminating the surfaces with light from a portion of the electromagnetic spectrum having a wavelength to which the additive is responsive, thereby rendering detectable the presence of the lane oil and the migration thereof over the bowling alley.

The method is described in conjunction with one exemplary embodiment which is deemed sufficient to effect a full disclosure of the subject invention. The exemplary method is described without attempting to show all of the various forms and modifications in which the invention might be embodied; the invention being measured by the appended claims and not by the details of the specification.

PREFERRED EMBODIMENT FOR CARRYING OUT THE INVENTION

Figure 1:
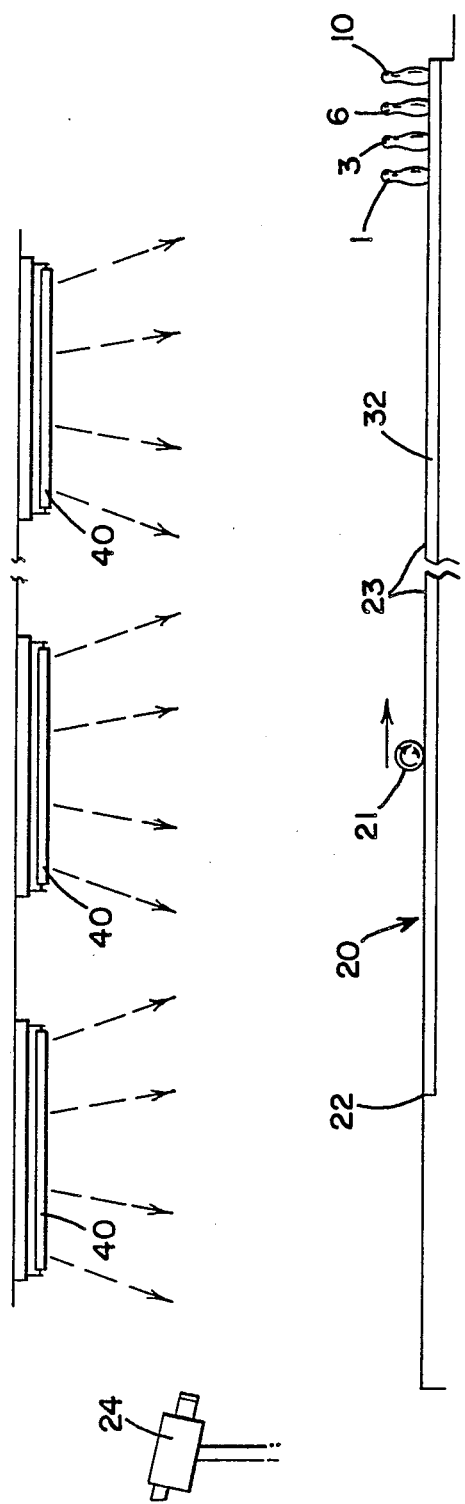
FIG. 1 is a schematic side elevation of a typical bowling lane depicting the equipment utilized to practice the method of the present invention.

With reference to FIG. 1, a bowling lane, indicated generally by the numeral 20 is depicted. The overall length of lane 20 is standard and has been partially broken away in order to depict the pins 1–10 and a ball 21 in play. The lane is of typical hardwood construction and is provided with a clear coat protective finish 23 along the entire length thereof and additionally carries a layer of lane oil from the foul line, 22 to a pre-determined distance toward the pins which varies among facilities. Thus, the area treated should not be construed as constituting any limitation on practice of the present invention. Of course, the protective finish cannot be seen apart from the underlying wood, as is true for the lane oil.

A television camera, indicated by the numeral 24 is located behind the bowler to present the off-premises viewer with the game as it is seen by the player. Of course, the position of the camera can be varied and multiple cameras (not shown) may be employed as desired by the broadcaster. While the camera 24 is normally present, the method of the present invention additionally employs the service of lamps 25, 26 and 27 which are mounted along the left and right sides of the lane and slightly above, as depicted in the drawing. Of course, lamps 25, 26 and 27 can also be mounted in or from the ceiling, directly over the lane surface 20 but greater wattage will be required. A greater description of the lamps 25, 26, 27 and their purpose shall be provided hereinbelow.

As was stated hereinabove, it is presently not possible to see the lane oil deposited on a bowling alley. The method of the present invention includes the step of incorporating an additive dye or tracer substance into the lane oil that is preferably only viewable when illuminated with light from a portion of the electromagnetic spectrum having a wavelength to which the additive is responsive. Such light is normally not present in conventional illumination, or it is present only in very low amounts and hence, the lane oil and additive is normally not discernable under ambient light.

Figure 2:
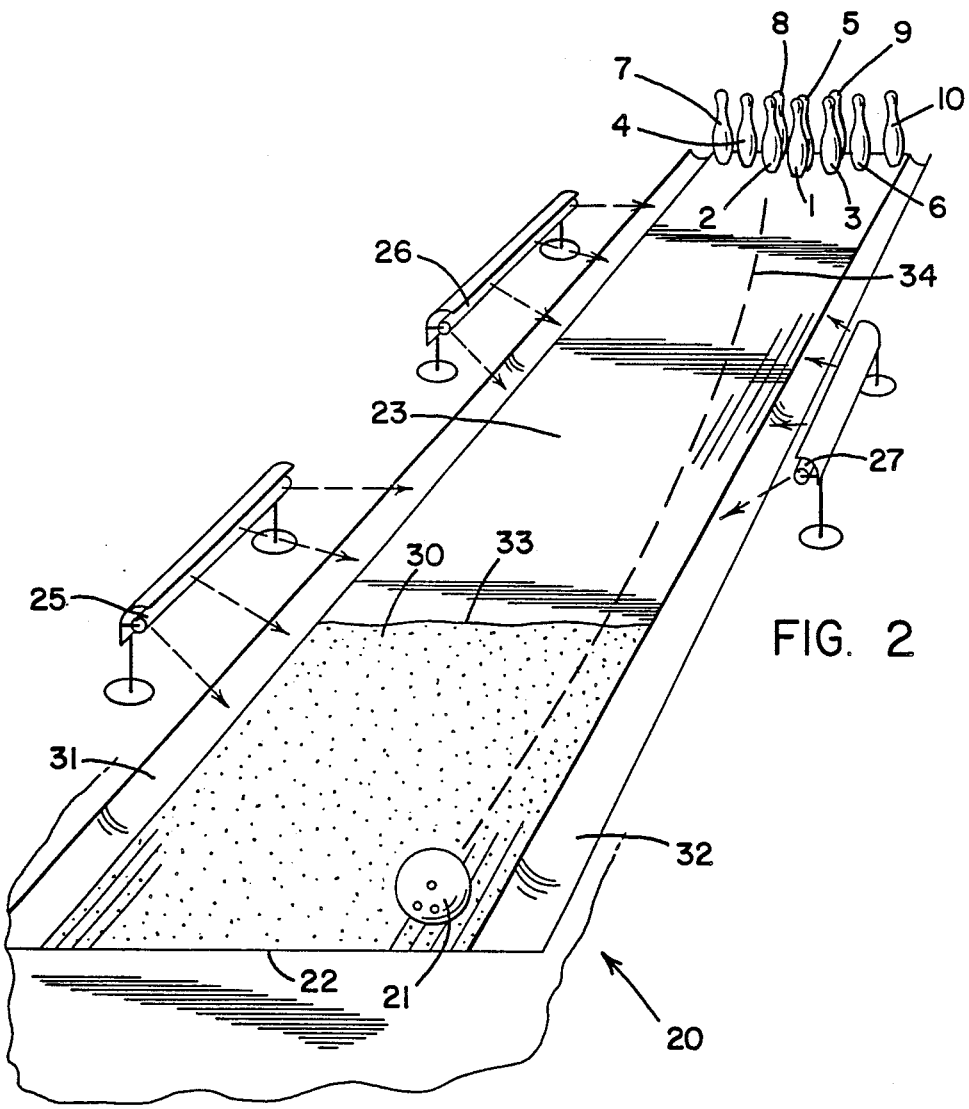
FIG. 2 is a schematic perspective view depicting the deposition of lane oil over the alley and the path that a bowling ball may take, passing therethrough for the first time.
Figure 3:
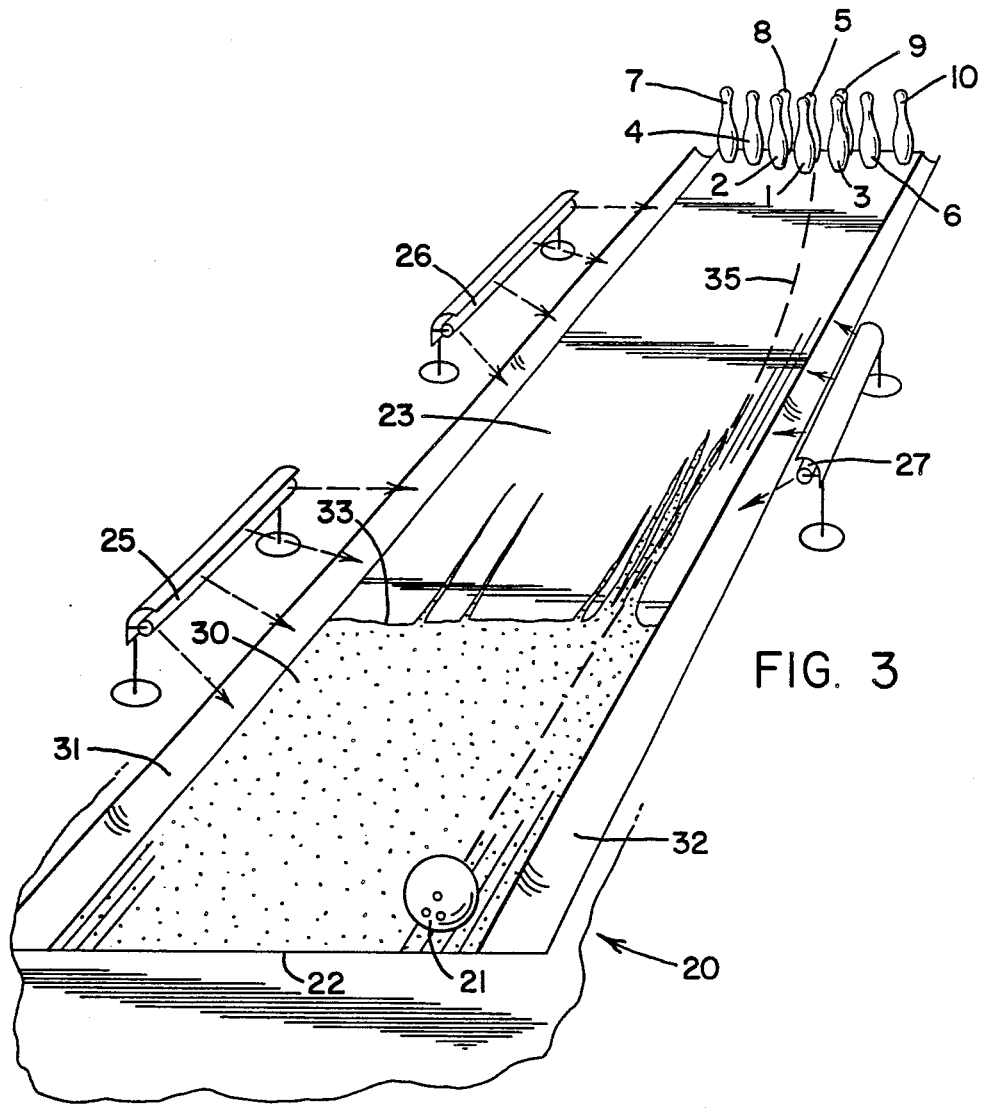
FIG. 3 is a similiar to FIG. 2, depicting the migration of lane oil along the alley after several bowling balls have been played.
Figure 4:
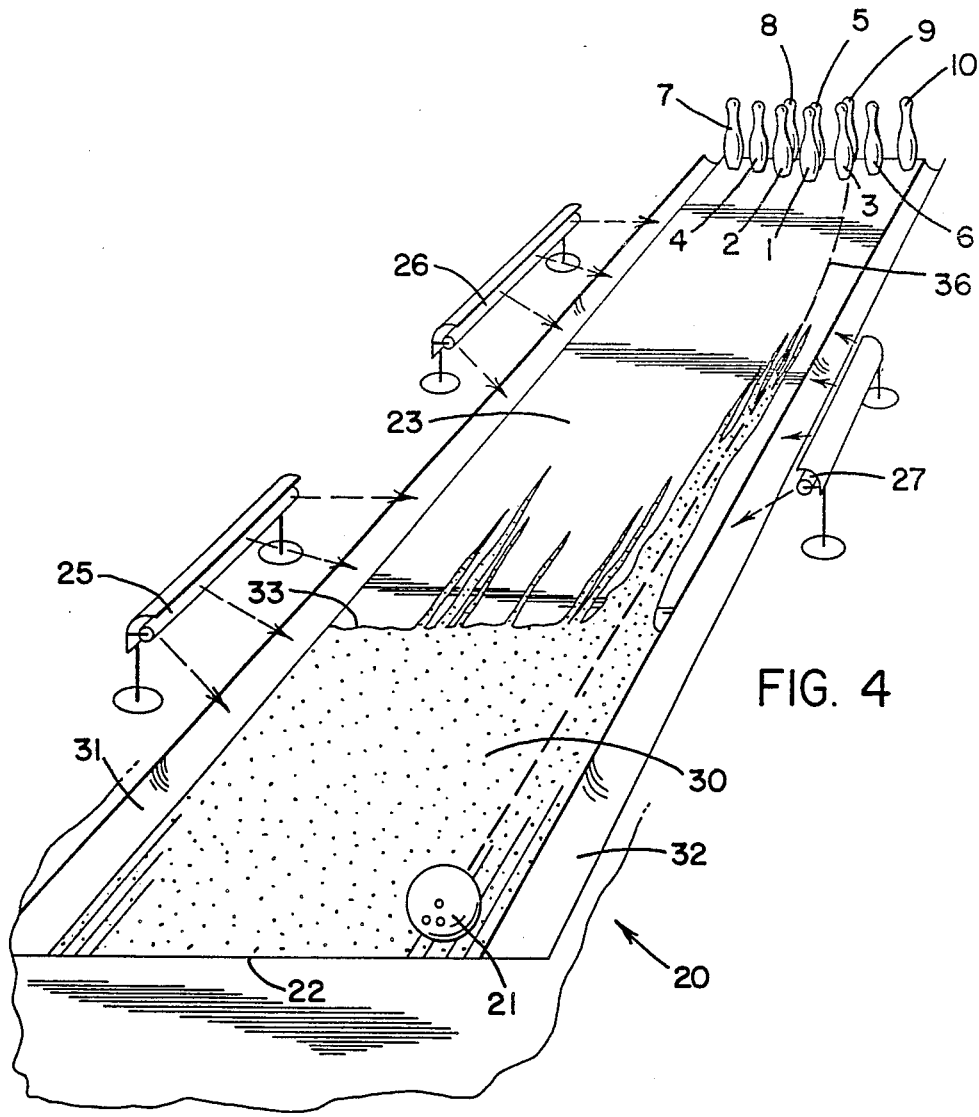
FIG. 4 is a schematic perspective view similar to FIGS. 2 and 3, depicting the migration of a greater amount of lane oil along the alley later in the game after many bowling balls have been played.

With reference to FIGS. 2-4, the lane oil has been rendered viewable and is depicted by the numeral 30. It extends across the width of the lane 20 from the left gutter 31 to the right gutter 32. It extends down the lane the standard distance, depicted by the numeral 33. Again it is to be understood that the oil is normally not visible to the player, the spectators or the television viewers; nor would it be viewable in the drawing figures. Nevertheless, in order to explain the method of the present invention, the oil has been given a stippled appearance so that its deposition and migration can be depicted.

In FIG. 2, the ball 21 is being played for the first time over a freshly oiled lane. Play of the ball has been represented as being delivered by a right handed player and the path the ball is anticipated to take is represented by the numeral 34. As delivered, the ball 21 will hook to the left, crossing the center of the lane, to strike the pins in a pocket, generally between pins 1 and 3.

In FIG. 3, several frames have been played and it is apparent that the oil 30 is being carried by the ball 21 down the lane. The migration is greater on the right side of the lane although a lesser amount is seen on the left side, indicating play of the ball to pick up spares. It will be noted that because of the migration of oil, a ball delivered substantially as in FIG. 2 will take a different path 35, striking between pins 1 and 3. The experienced bowler cannot actually see the oil but he observes the modification in the ball path and thus, will adjust his delivery in order to compensate therefor.

In FIG. 4, many frames into the game, the oil has been carried to a much greater extent down the lane and along the right side. Again, assuming the same delivery as depicted in FIg. 2, the ball has taken yet another path 36 and will now strike the pin 3. Of course, the bowler may further adjust his delivery to the extent possible in order to achieve a path he or she finds more desirable. By comparing each of the successive paths 34-36, it will be apparent that the ball 21 is losing its hook because the area of total frictional engagement between the ball and the lane 20, that is free from oil, is lessened during later play.

Because professional bowlers are not able to see the migration of the oil, as play progresses, they perform all of the foregoing judgements based upon experience and visual feedback from play. Television viewers and spectators, live at play, are also not directly aware of the oil spread and therefore, do not understand the apparent erratic behavior of the balls. Commentators for televised play attempt to explain the action of the oil and consequent choices of balls and ball delivery.

The method of the present invention allows the oil 30 and its migration to be seen. In the preferred embodiment, a dye or other substance that is responsive to the ultraviolet portion of the electronic magnetic spectrum is mixed with the lane oil prior to its application to the lane 20. These tracer substances contain compounds that become illuminated under ultraviolet length which, in turn, illuminates the lane oil. One such product that is commercially available is manufactured by U.V.P., Inc. under the name BLAK-RAY ®. It is a known product which has been utilized in contact with human skin for marking purposes and thus, should present no health hazard to either the bowlers or to the lane caregivers. Additionally, its effect on the oil and the behavior of the oil is expected to be and should be negligible. Amounts of the substance that will be mixed with the oil can be determined somewhat empirically to obtain a discernable or "viewable" oil under ultraviolet length. The latter is, in turn, a function of the number of ultraviolet lights e.g. 25, 26, that are employed; their wattage and, their distance from the surface of the lane 20.

With reference again to FIG. 2, the lights 25, 26 and 27 would provide ultraviolet illumination. The house lights 40, providing conventional, ambient illumination, could be shut down during commercials for as little as a few seconds to allow "stills" to be taken of the lane by special cameras. These stills could then be utilized as the play progresses. Properly equipped with filters and the like, the television camera 24 could be employed to view the lane oil and tracer substance and display it in a split screen fashion or window on the television screen or as an overlay of the lane. Spectators in the house and television viewers could see the actual paths of oil deposited by the balls and begin to understand the effect thereof on play. Television viewers could also view past shots, selected by the broadcaster, and see where the ball diverged from the oil and made greater lane contact. This would allow the commentator to explain greater or less hook and other ball behavior.

As a variation, by employing proper filtration, real-time monitoring of the play by specially equipped cameras 24, could be practiced. As an advantage, this could be less disruptive than shutting down the house lights 40 and, if it were decided to be against the rules for the bowler to be permitted to see the oil migration, the same would remain invisible at the game but would be visible only to viewers of closed circuit and television broadcasts. As a disadvantage, real time monitoring may result in less contrast, an increase in equipment costs or both and, it would not affor the view to the spectators live at the tournament.

While the method of the present invention may be particularly useful in conjunction with professional bowlers playing in tournaments, it could also be utilized for instructional purposes. Thus, it would be possible for non-professional bowlers to see the actual migration of oil during their games. Alternatively, bowlers could replay video taped play of a professional tournament narrated by an instructor.

Although the method of the present invention has been described in conjunction with the use of ultraviolet illumination, it should be appreciated that it can also be practiced under the infra-red portion of the electromagnetic spectrum by selection of a different additive dye or tracer substance responsive to intra-red wavelengths of light. Such substances are generally known and thus, practice of the method is not limited to any specific compound.

In conclusion, it should be apparent that the method of the present invention satisfies the foregoing objects by providing a relatively simple to use and understand manner for visually displaying the migration of lane oil during bowling tournaments. Of course, the foregoing method is not necessarily limited to bowling tournaments and can just as readily be set up for recording and television of non-tournament play and practice sessions which may be utilized for various training.

Moreover, although the method has been exemplified by the use of an ultraviolet light, it is within the skill of the art to employ other dyes, additives, or tracer substances to display the lane oil. Similarly, combinations of filters and lights may be employed to aid with the illumination of the oil. Thus, practice of the present invention is not limited solely to the description of the preferred embodiment.

It is therefore, to be understood that any variations evident fall within the scope of the claimed invention and that the selection, placement and utilization of specific equipment as well as the dyes and other tracer substances can be determined without departing from the spirit of the invention herein disclosed and described. Moreover, the scope of the invention shall include all modifications and variations that may fall within the scope of the attached claims.

I claim:

1. A method for displaying the migration of lane oil over bowling alleys during play comprising the steps of:
   incorporating an additive into the lane oil that is non-discernable when viewed with ambient light;
   applying said lane oil and incorporated additive to the surfaces of a bowling alley in a conventional manner; and
   selectively illuminating said surfaces with light from a portion of the electromagnetic spectrum having a wavelength to which said additive is responsive, thereby rendering detectable the presence of said lane oil and the migration thereof over the bowling alley.

2. A method, as set forth in claim 1, including the additional step of broadcasting said surfaces selectively illuminated with light having a wavelength to which said additive is responsive.

3. A method, as set forth in claim 2, wherein said step of broadcasting is conducted with a television camera.

4. A method, as set forth in claim 3, including the additional step of controlling said ambient light and said light having a wavelength to which said additive is responsive in order to render detectable the presence of said additive in the lane oil under ambient light.

5. A method as set forth in claim 3, including the additional step of dimming said ambient light projected onto the bowling alley prior to said step of selectively illuminating.

6. A method, as set forth in claim 3, including the additional step of terminating the source of ambient light projected onto the bowling alley during said step of selectively illuminating.

7. A method, as set forth in claim 2, whereins said step of broadcasting includes the step of superimposing said detectable presence of lane oil over the regular broadcast of play.

8. A method, as set forth in claim 2, wherein said step of broadcasting includes the step of providing said detectable presence of lane oil in a split screen fashion or window on a television screen separated from the regular broadcast of play.

9. A method, as set forth in claim 1, wherein said additive is selected from the group consisting of dyes responsive to wavelengths of light in the infra-red portion of the spectrum.

10. A method, as set forth in claim 1, wherein said dye is responsive to wavelengths in the ultraviolet portion of the spectrum.

11. A method as set forth in claim 10, wherein said step of selectively illuminating includes the steps of locating at least one ultraviolet lamp relative to the bowling alley containing said lane oil and incorporated additive; and energizing said lamp to the extent necessary to render said incorporated additive and lane oil visible.

* * * * *